United States Patent [19]

Burton

[11] Patent Number: 4,659,863

[45] Date of Patent: Apr. 21, 1987

[54] PHENOLIC ESTER SYNTHESIS

[75] Inventor: Lester P. J. Burton, Baton Rouge, La.

[73] Assignee: Ethyl Corporation, Richmond, Va.

[21] Appl. No.: 775,166

[22] Filed: Sep. 12, 1985

[51] Int. Cl.$^4$ ............................................. C07C 69/76
[52] U.S. Cl. ...................................................... 560/75
[58] Field of Search ........................................... 560/75

[56] References Cited

U.S. PATENT DOCUMENTS

| 3,285,855 | 11/1966 | Dexter et al. | 560/75 |
| 4,085,132 | 4/1978 | Park et al. | 560/75 |
| 4,228,297 | 10/1980 | Haeberli et al. | 560/75 |
| 4,529,809 | 7/1985 | Irving et al. | 560/75 |

Primary Examiner—Werren B. Lone

Attorney, Agent, or Firm—Donald L. Johnson; John F. Sieberth; J. D. Odenweller

[57] ABSTRACT

A process which enhances conversion and speeds the reaction rate for the preparation of esters. Methyl acrylate and a hindered phenol are reacted (i) in the presence of an alkali metal alkaline catalyst that provides a phenolate anion and (ii) in the presence of an agent which solubilizes the phenolate to enhance the reaction rate. Excellent yields of methyl ester are obtained in a rapid reaction and by-products are minimal. The invention includes a preparation of methyl $\beta$-(3,5-dialkyl-4-hydroxyphenyl)propionates by reaction of a hindered phenol with methyl acrylate in the presence of an alkaline catalyst and dimethyl sulfoxide present in an amount sufficient to advance the reaction rate.

24 Claims, 2 Drawing Figures

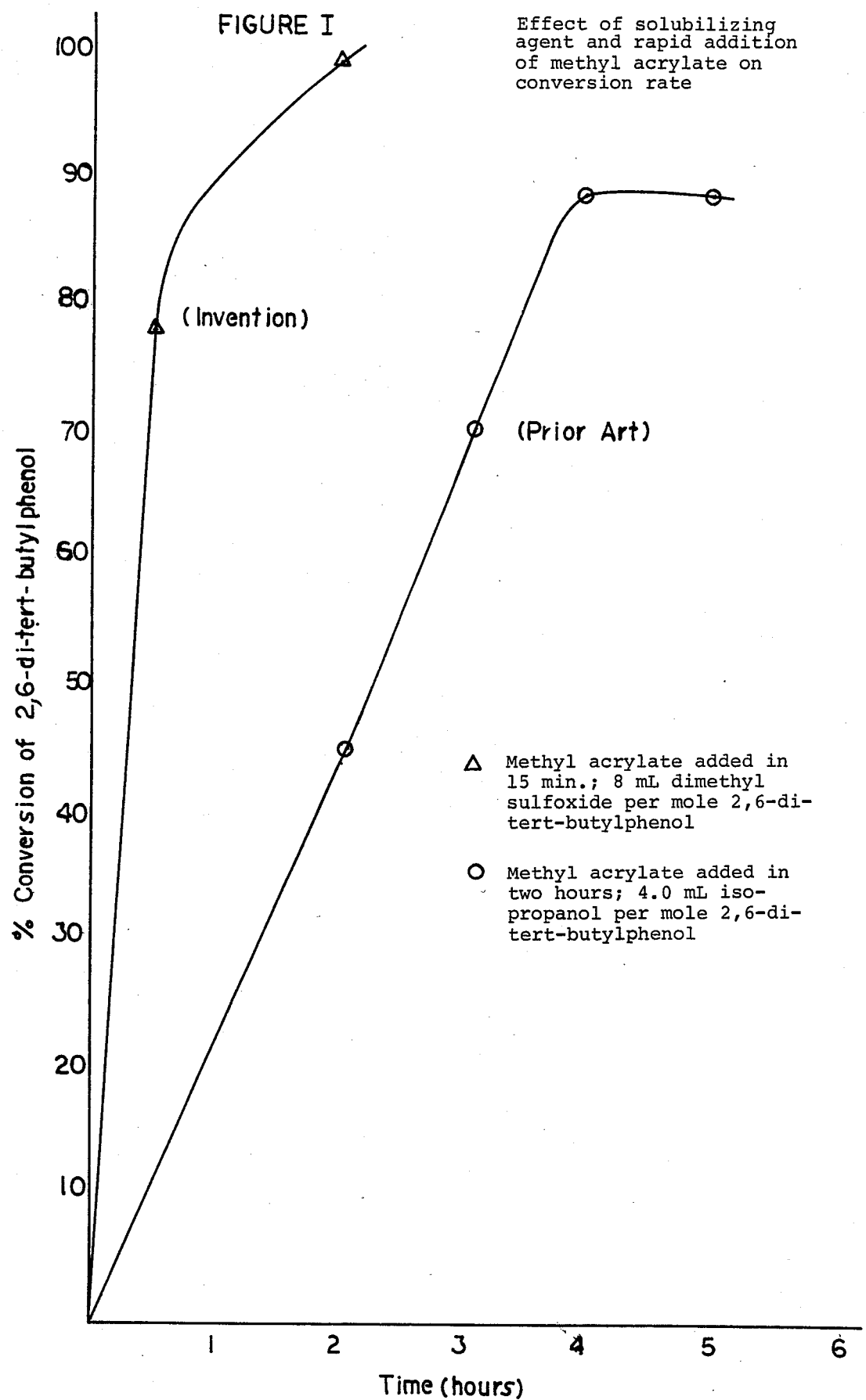

FIGURE II
Effect of solubilizing agent and rate of addition on by-product formation
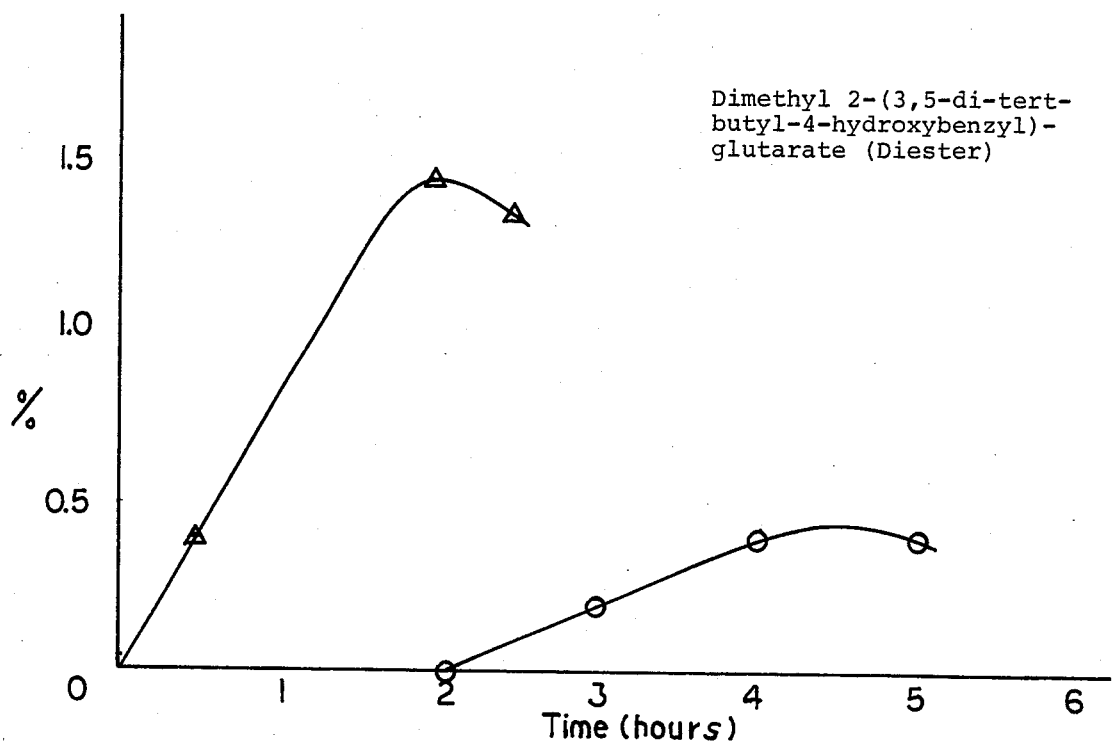
Dimethyl 2-(3,5-di-tert-butyl-4-hydroxybenzyl)-glutarate (Diester)
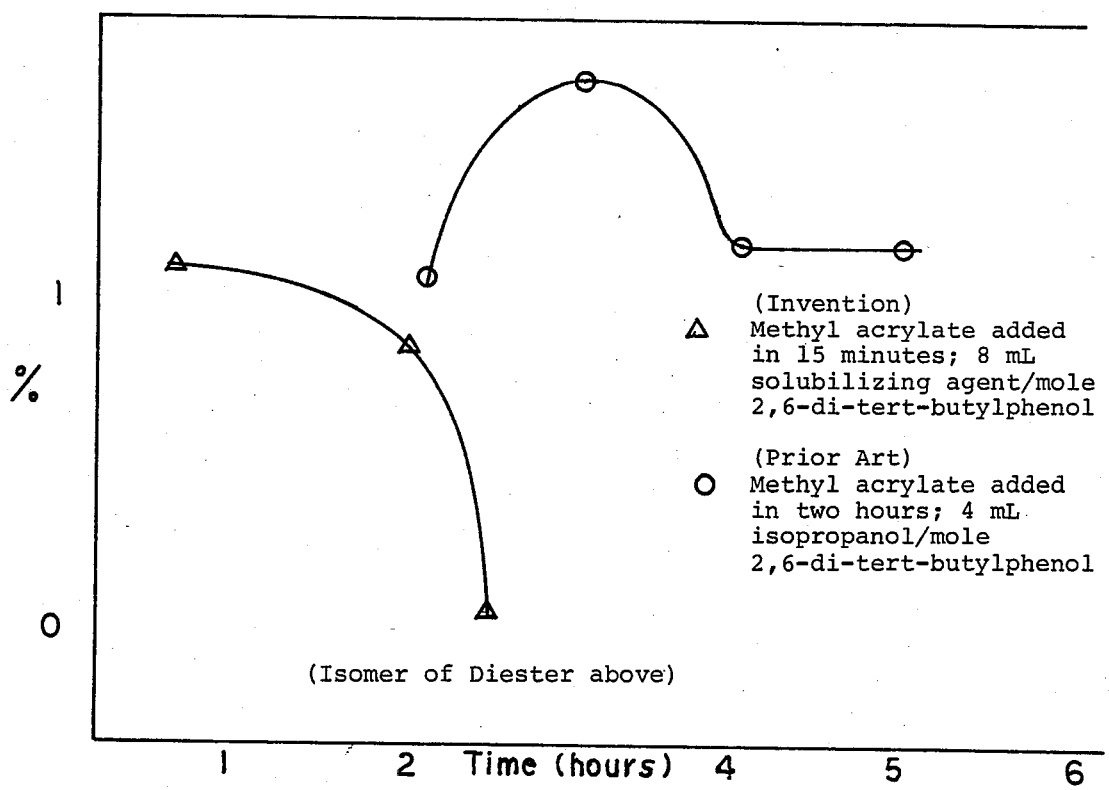
(Invention)
△ Methyl acrylate added in 15 minutes; 8 mL solubilizing agent/mole 2,6-di-tert-butylphenol
(Prior Art)
O Methyl acrylate added in two hours; 4 mL isopropanol/mole 2,6-di-tert-butylphenol
(Isomer of Diester above)

PHENOLIC ESTER SYNTHESIS

BACKGROUND OF THE INVENTION

This invention relates in general to antioxidants and in particular to processes for the preparation of alkyl ester antioxidants containing a hindered phenol moiety.

Known methods for the production of higher alkyl hydroxy alkylphenyl alkanoate esters require several steps usually including transesterification of a lower alkyl ester to a higher ester. The lower alkyl esters are first prepared from a hindered phenol and methyl acrylate in a fashion which either produces large amounts of by-products or requires substantial amounts of suitable solvents to remove the by-products. Other known methods require very slow reaction between the methyl acrylate and the hindered phenol so as to circumvent the shortcomings of the previously mentioned methods. However, these methos require the very slow addition to methyl acrylate to the reaction mixture which detracts from the economy of the process. Also the reaction rates are slow despite the use of small amounts of alcohols or solvents. Suggestions have been made to improve the conversion of the prior art processes but a process is needed which provides a good conversion of high purity product with a relatively fast reaction.

SUMMARY OF THE INVENTION

The present invention is an improved process for the production of methyl esters of hindered phenol derivatives by reacting a hindered phenol with methyl acrylate, preferably but not necessarily by rapid addition of the methyl acrylate to a reaction mixture containing a hindered alkylphenol anion, in the presence of an alkaline catalyst and a reaction rate increasing portion of a solubilizing agent.

According to the process of the invention, the reaction may be carried out with rapid addition of methyl acrylate but this is not necessary to obtain the benefits of using the solubilizing agent of the invention.

BRIEF DESCRIPTION OF THE DRAWINGS

FIG. 1 is a plot of the effect of solubilizing agent and rapid addition of methyl acrylate on the conversion rate of the reaction between a hindered phenol and methyl acrylate in the presence of alkaline catalyst. FIG. I also compares the improved process of the present invention to the slow reaction rate process of the prior art.

FIG. II is a plot of the effect of rate of addition of methyl acrylate and use of a solubilizing agent on the formation of significant by-products. FIG. II also compares the formation of by-products according to the invention with the formation of by-products according to the process of the prior art.

DESCRIPTION OF THE PREFERRED EMBODIMENTS

A preferred embodiment of the present invention is a process for the preparation of a methyl ester of the formula I:

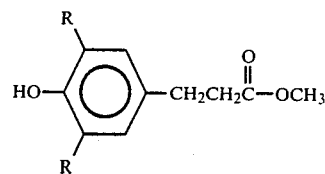

wherein the R are independently selected alkyl, cycloalkyl, aryl, alkaryl, or aralkyl preferably having 1 to 12 carbon atoms, comprising (a) providing in a reaction mixture of about one mole part methyl acrylate and about one mole part phenol of formula II:

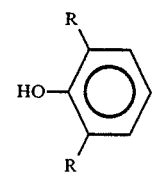

an alkali metal alkaline catalyst so as to form in said reaction mixture an alkali metal phenolate reactive intermediate of structure III:

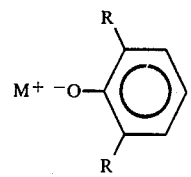

wherein M+ is an alkali metal cation; and (b) reacting said reaction mixture in the presence of at least about 0.10 mole parts of an agent to solubilize said alkali metal phenolate and increase the rate of reacting said reaction mixture.

The process of the present invention provides an improved method of obtaining methyl alkanoate esters containing hydroxy alkylphenyl groups in a manner which produces good yields of product and a minimal amount of undesirable by-products.

Other alkyl alkanoate esters containing hydroxy alkylphenyl groups may be produced by reacting a hindered phenol with an acrylate having the structure:

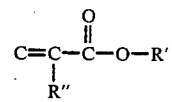

wherein the R' is any of various alkyl groups, preferably of 1 to 20 carbon atoms and the R" is H or any of various alkyl groups, preferably of 1 to 20 carbon atoms, more preferably of 1 to 4 carbon atoms. Examples are ethyl acrylate, isopropyl acrylate, and methyl methacrylate.

According to the invention, hindered phenols are reacted to prepare the desired esters. The hindered phenols of the invention include compounds having the formula II:

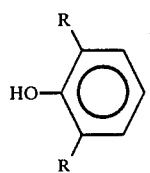

(II)

wherein the R are independently selected from alkyl, cycloalkyl, aryl, alkaryl, or aralkyl groups. Preferably, the alkyl groups contain 1 to 12 carbon atoms, the cycloalkyl groups contain 5 to 8 carbon atoms, the aryl groups contain 6 to 12 carbon atoms, and the alkaryl or aralkyl groups contain 7 to 12 carbon atoms. The preferred substituents for the phenol of the invention are alkyl groups of 1 to 12 carbon atoms, more preferably alkyl groups of 1 to 4 carbon atoms, still more preferably branched alkyl groups and most preferably α-branched alkyl groups of 3 or 4 carbon atoms. The most preferred phenol is 2,6-di-tert-butylphenol. Other suitable reactant phenols are 2-methyl-6-tert-butylphenol; 2,6-diisopropylphenol; 2,6-di-sec-butylphenol; 2-methyl-6-ethylphenol; 2,6-diethylphenol; 2-isopropyl-6-tert-butylphenol; 2,6-dicyclopentylphenol; 2,6-dicyclohexylphenol; 2,6-di(α-methylbenzyl)phenol; 2-methyl-6-(α,α-dimethylbenzyl)phenol; 2,6-dibenzylphenol; 2,6-diphenylphenol; and the like. Optionally, the 2,6-di-substituted phenols of the invention may also have 3- and 5-substituents which do not adversely affect the reaction.

The alkaline catalysts of the invention include the alkali metal hydrides, alkali metal hydrocarbyloxides, alkali metal hydroxides, and alkali metal amides. The alkali metal hydrocarbyloxides include those having the formula

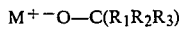

wherein M is an alkali metal ion, and the $R_1$, $R_2$, and $R_3$ are independently selected from hydrogen and alkyl, cycloalkyl, aryl, aralkyl, and alkaryl groups, preferably having 1 to 12 carbon atoms or $R_1$ and $R_2$ taken together can form a cycloalkyl ring of 5-8 carbon atoms. Of these the alkali metal alkoxides where $R_1$ is alkyl of 1-12 carbon atoms and $R_2$ and $R_3$ are hydrogen are more preferred. The alkali metal amides of the invention are those of the formula

wherein M, $R_1$, and $R_2$ are as defined above.

The alkyl radicals suitable for $R_1$ and $R_2$ include methyl, ethyl, isopropyl, sec-butyl, tert-butyl, and higher carbon alkyl groups. The aryl groups include phenyl and the aralkyl groups include benzyl. The cycloalkyl groups include cyclopentyl, cyclohexyl, and the like.

Suitable alkali metals for the alkaline catalyst of the invention are lithium, sodium, potassium, rubidium, and cesium.

The alkaline catalysts of the invention include sodium hydride, potassium hydride, and lithium hydride. The alkaline catalysts of the invention also include the alkali metal alkoxides such as sodium methoxide, potassium methoxide, lithium methoxide, potassium propoxide, sodium isopropoxide, potassium tert-butoxide, sodium 1,1-dimethylbutoxide, potassium benzyloxide, sodium benzylisopropoxide, and the like.

Also included as catalysts of the invention are the amides such as lithium N-methylamide, sodium N-ethylamide, lithium N,N-dimethylamide, and sodium N-methyl-N-phenylamide. Preferred among the amide catalysts are those sodium and potassium amides where $R_1$ and $R_2$ represent hydrogen.

The most preferred alkaline catalyst of the invention is potassium tert-butoxide. Generally, potassium alkoxide catalysts are preferred.

The alkaline catalysts, when added in sufficient amount, form a reactive species which may be considered an intermediate. This specie is an anion which can conveniently be described by the following resonance forms:

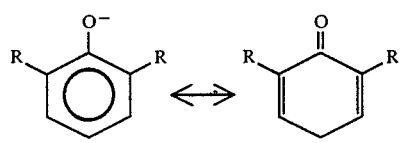

I have determined that increasing the concentration of alkaline catalyst to a certain maximum, which maximum depends upon the catalyst used, improves the conversion of alkylated phenol although the reaction rate of the process of the invention is not significantly affected by such increase. A suitable range of amount of alkaline catalyst for the reaction is about 0.001 to 10 mole percent based on the amount of hindered phenol reacted. A range of about 0.01 to 1 mole percent is preferred and a more preferred range is about 0.02 to 0.5 mole percent based on the amount of phenol, but depending upon the particular catalyst used.

For example, the reduction of the amount of potassium tert-butoxide catalyst from 2.8 grams (0.025 mol) per mole of 2,6-di-tert-butylphenol to about 2 grams per mole of phenol decreases the final conversion from about 99% to about 95% in a 2 hour (rapid methyl acrylate addition) reaction.

The amount of solubilizing agent employed must be at least adequate for the catalyst used. There must be present sufficient mole parts of the solubilizing agent per mole part catalyst. A broad range is usable depending upon the agent and catalyst chosen. For example, with dimethyl sulfoxide and potassium tert-butoxide a mole ratio of at least about 4:1, respectively, is optimum. More or less agent may be used in any case.

Various sources of methyl acrylate may be used for the invention but a relatively pure grade of reactant methyl acrylate is preferred. The methyl acrylate has the emperical formula

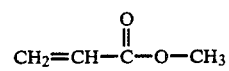

According to the process of the invention, the hindered phenol of the invention is first rendered liquid by melting and the alkaline catalyst is added. For example, a reaction quantity of 2,6-di-tert-butylphenol is heated to about 60°-65° C. or higher under vacuum to purge oxygen. The entire reaction is preferably carried out in an atmosphere of inert gas, preferably nitrogen. After the hindered phenol is melted, the desired alkaline catalyst and solubilizing agent of the invention are added.

The mixture is then heated to a reaction temperature and the methyl acrylate is added, preferably at a rapid rate such as 15 minutes (a normal pumping rate for large scale reactors) rather than gradually over 2 hours or more. A suitable range of times for adding the methyl acrylate to the reactant hindered phenol slurry is all at once, where feasible, to a period of about 15-60 minutes or preferably 15-30 minutes, slightly longer where pumping at such a rate is convenient. Of course the invention with its advantages of using an effective amount of a solubilizing agent to increase the reaction rate may be carried out with slow addition of methyl acrylate.

I have experimentally determined that increasing the rate of addition of methyl acrylate either permits or causes the reaction rate to increase as measured by conversion of reactant alkylated phenol.

The above described process may be carried out in any order of addition of reactants but it is preferable to add the methyl acrylate to the mixture of hindered phenol, catalyst, and solubilizing agent.

The solubilizing agents of the invention have been found to accelerate the rate of conversion of the hindered phenol to an ester of the invention. The solubilizing agents of the invention include aprotic polar solvents such as dimethyl sulfoxide, dimethylformamide and other dialkyl sulfoxides and formamides. The solubilizing agents also include phase transfer catalysts such as tris(3,6-dioxaheptyl)amine also called TDA-1 phase transfer agent as sold by Rhone-Poulenc $((N(CH_2CH_2OCH_2CH_2OCH_3)_3)$. Various other phase transfer catalysts and aprotic solvents may be used. Other classes of solubilizing agents include the crown ethers such as 1,4,7,10,13-pentaoxacyclopentadecane (15-Crown-5); 1,4,7,10,13,16-hexaoxacyclooctadecane (18-Crown-6); 1,4,7,10-tetraoxacyclododecane (12-Crown-4); dibenzo-18-crown-6-dibenzyl-24-crown-8; dicyclohexano-18-crown-6; dicyclohexano-24-crown-8; and the like. Another agent suitable for the invention is sulfolane(tetramethylene sulfone).

The use of the solubilizing agents of the invention permits rapid addition of methyl acrylate while still obtaining enhanced conversion, unexpectedly increased reaction rate, and minimal production of by-products.

The amount of solubilizing agent used according to the invention may vary over a broad range. A suitable range for the amount of solubilizing agent is at least about 0.10 molar part to 1.00 mole part per mole of hindered phenol reactant.

The solubilizing agents of the invention are effective to solubilize the alkali metal phenolate formed by the alkaline catalyst of the invention and thereby increase the rate of reaction in the reaction mixture. The most preferred phenolate solubilizing agent of the invention is dimethyl sulfoxide ($CH_3SOCH_3$). The use of dimethyl sulfoxide and potassium tert-butoxide according to a preferred embodiment of the process of the invention results in the production of the desired product in a conversion of over 99% in less than 2 hours.

By comparison, a prior art process required at least 2 hours just for the addition of the methyl acrylate reactant. The process of the invention permits rapid production of the product of the invention. The phenolate solubilizing agent of the invention unexpectedly results in an increase in the reaction rate of the invention thereby enhancing the overall economy of production of esters which are used as an antioxidant or as a chemical intermediate for production of antioxidants and other products. For example, the utility of the methyl 3-(3,5-dialkyl-4-hydroxyphenyl)propionate of the invention to make the commercial antioxidant octadecyl 3-(3,5-di-tert-butyl-4-hydroxyphenyl)propionate is well known.

A further advantage of the invention, compared to the prior art, is that an excellent yield of the desired product is obtained, optionally in a much shorter period of time, while resulting in the production of an even smaller amount of undesirable by-products.

Generally, about equimolar portions of reactants are used according to the invention. Either of the reactants, methyl acrylate or hindered phenol, may be used in excess according to the process of the invention but a slight excess of methyl acrylate is preferred. The unreacted methyl acrylate is readily stripped from the reaction mixture. The reaction mixture may then be quenched with various agents to render the product in a suitable form for handling or further reaction. Such agents include acetic acid, hydrochloric acid, and sulfuric acid.

A suitable range of temperatures for the reaction is about 75°-180° C., preferably 100°-160° C. When using dimethyl sulfoxide and a potassium tert-butoxide alkaline catalyst, the preferred reaction temperature is about 100°-160° C. The temperature of the reaction mixture may drop slightly with the addition of the methyl acrylate but it generally then rises due to the exothermic nature of the reaction. Excess methyl acrylate is readily stripped off by vacuum and the mixture is easily neutralized with a small amount of glacial acetic acid before cooling. The reaction progress may be readily monitored by gas chromatographic methods.

A better understanding of the invention will be had by a review of the drawing figures and a comparison of the following examples.

COMPARATIVE EXAMPLE

Slow Addition of Methyl Acrylate

Under a nitrogen atmosphere, 103.0 grams (0.499 mol) 2,6-di-tert-butylphenol was melted at about 70° C. in a round bottom flask. A 1.4 gram (0.012 mol) portion of potassium hydroxide and 2 mL isopropyl alcohol (0.012 mol) were added to form a pale green slurry. The slurry was heated to 108° C. and 50 mL (0.56 mol) methyl acrylate (containing 200 ppm p-methoxyphenol) was gradually added dropwise over two hours. Intermittent samples for gas chromatography analyses were taken. After 5 hours at 107°-108° C. the mixture was neutralized with 0.6 mL glacial acetic acid. A plot depicting the reaction rate as measured by percent conversion of 2,6-di-tert-butylphenol (to methyl-$\beta$-(3,5-di-tert-butyl-4-hydroxyphenyl)propionate) appears as the rightmost plot in FIG. I. A plot of significant by-product formation appears in FIG. II. This comparative example is represented as Run No. 1 in the table following the example below.

EXAMPLE

Rapid Addition of Methyl Acrylate with Solubilizing Agent

Under nitrogen, 206.4 grams (1.00 mol) of 2,6-di-tert-butylphenol were melted, heated to 60°-65° C., and placed under vacuum. The vacuum was broken with nitrogen and 2.8 grams (0.025 mol) of potassium tert-butoxide and 8 mL (0.11 mol) of dried dimethyl sulfoxide, $CH_3SOCH_3$, were added. The slurry was heated to 110° C. and 100 mL (1.11 mol) of methyl acrylate was dripped steadily in within 15 minutes. The temperature dropped to 107° C. before slowly rising to 135° C. in 35 minutes. After 1 hour, the temperature had dropped to 110° C. and an additional 5 mL portion of methyl acrylate was added. After 2 hours, vacuum was applied to strip off excess methyl acrylate. After a total of 2½ hours, the mixture was quenched with 2.5 mL glacial acetic acid and allowed to cool. The reaction rate and conversion are plotted in FIG. I (leftmost plot) for comparison. Similarly, a plot of significant by-product formation appears in FIG. II. The conversion to desired product and identity of by-products were confirmed by NMR and GL/mass spectrometry. This example is represented as Run No. 7 in the table below.

From a comparison of the plots in FIGS. I and II, it can be seen that an excellent conversion of product may be achieved with a rapid reaction rate bypassing the shortcomings of the prior art process requiring slow addition.

I found that the detectable by-products in preparation of methyl-β-(3,5-di-tert-butyl-4-hydroxyphenyl)propionate by the method of the invention and the prior art method are:
isopropyl β-(3,5-di-tert-butyl-4-hydroxyphenyl)propionate;
an isomer of methyl β-(3,5-di-tert-butyl-4-hydroxyphenyl)propionate of unknown structure;
dimethyl 2-(3,5-di-tert-butyl-4-hydroxybenzyl)glutarate (a diester); and
an isomeric diester of unknown structure.

The last two mentioned compounds were the only by-products present in a significant amount. Mass spectrometry, H-NMR spectroscopy, and infrared analyses were used to identify the type and amount of by-products as best possible.

The by-products formed more rapidly with faster methyl acrylate addition but unexpectedly, and contrary to the teaching of the prior art, the final concentration of total by-products was no worse than with gradual addition of methyl acrylate. FIG. II depicts by-product formation for the significant compounds. The sum of by-products at reaction end for a reaction with rapid addition of methyl acrylate and using an effective amount of solubilizing agent is somewhat less than the sum of by-products at reaction end for a reaction with gradual addition of methyl acrylate and adding a small amount of isopropanol.

A series of experimental runs was conducted with isopropanol and solubilizing agents of the invention. The results of the experimental runs are summarized in the table below.

| Run No. | Additive | Volume of Agent per mol of phenol[1] (mL) | Time for methyl acrylate addition (hours) | Time to reach 90% conversion of phenol[1] (hours) |
|---|---|---|---|---|
| 1 | Isopropanol | 4 | 2 | 4½ |
| 2 | Isopropanol | 4 | ¾ | 4 |
| 3 | Isopropanol | 8 | 1 | 4 |
| 4 | Dimethyl sulfoxide | 8 | 1 | 1¾ |
| 5 | Dimethylformamide | 8 | 1 | 1¾ |
| 6 | TDA-1[2] | 6 | ¼ | 2 |
| 7 | Dimethyl sulfoxide | 8 | ¼ | ⅞ |

[1]2,6-di-tert-butylphenol
[2]tris(3,6-dioxaheptyl)amine

Run No. 1 is a process suggested by the disclosure of U.S. Pat. No. 4,228,297. The use of small amounts (4 mL/mole phenol) of isopropanol is shown to give a slight improvement in total conversion of the phenol. However, more rapid addition of methyl acrylate (using isopropanol) in Run No. 2 and use of an even larger portion of isopropanol in Run No. 3 did not significantly advance the reaction rate. Thus, isopropanol is inefficient as a solubilizing agent.

Run No. 4 and Run No. 5 demonstrate that the use of a relatively large amount of dimethyl sulfoxide (0.11 mol) or dimethylformamide (0.10 mol) per mole reactant phenol, even at the moderate addition time of one hour, drastically advances the reaction rate such that a 90% conversion of 2,6-di-tert-butylphenol (primarily to methyl 3-(3,5-di-tert-butyl-4-hydroxyphenyl)propionate) is achieved in less than two hours.

Run No. 6 demonstrates that the use of an amine phase transfer agent is also an efficient solubilizing agent to significantly advance the reaction rate.

Finally, Run No. 7 demonstrates that the increased reaction rate from the use of efficient solubilizing agent is further enhanced by the rapid addition of reactant methyl acrylate.

According to the invention, the desired ester products are obtained in high yields and substantially free of undesirable by-products. They may be used for stabilization of organic materials or as a chemical intermediates to the production of known antioxidants and the like.

Having described the process which I regard as my invention, it should be recognized that changes and variations within the scope and spirit of the invention can be made by one skilled in the art and it is accordingly to be understood that the present description of the invention be limited only by the lawful scope of the following claims.

I claim:

1. A process for the preparation of excellent yields of a methyl ester of formula I:

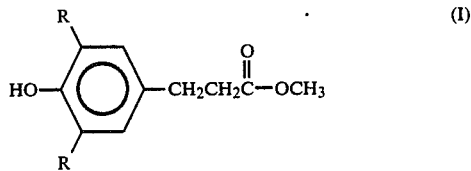

wherein the R are independently selected from alkyl having 1–12 carbon atoms, cycloalkyl have 5–8 carbon atoms, aryl having 6–12 carbon atoms, and alkaryl or aralkyl having 7 to 12 carbon atoms, consisting essentially of (a) providing in a reaction mixture of about one mole part methyl acrylate and about one mole part phenol of formula II:

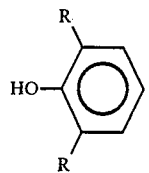 (II)

wherein R is as defined above, an alkali metal alkaline catalyst so as to form in said reaction mixture an alkali metal phenolate reactive intermediate and (b) reacting said reaction mixture in the presence of at least about 0.10 mole part of an agent effective to solubilize said alkali metal phenolate and effective to increase the rate of reacting said reaction mixture; wherein said methyl acrylate is added to said phenol in step (a) in a period of less than 60 minutes and the formation of undesirable by-products is reduced.

2. The process of claim 1 wherein said solubilizing agent is selected from the group consisting of aprotic polar solvents, phase transfer catalysts, and crown ethers.

3. A process of claim 1 wherein said alkali metal alkaline catalyst is an alkali metal alkoxide.

4. The process of claim 3 wherein said alkali metal alkoxide is potassium tert-butoxide.

5. The process of claim 1 wherein said reaction mixture is reacted at about 75°–180° C.

6. The process of claim 1 wherein the Rs are tert-butyl.

7. The process of claim 1 wherein said agent to solubilize said alkali metal phenolate is an aprotic polar solvent.

8. The process of claim 7 wherein said aprotic polar solvent is dimethyl sulfoxide.

9. The process of claim 7 wherein said aprotic polar solvent is dimethylformamide.

10. The process of claim 1 wherein said agent to solubilize said alkali metal phenolate is a phase transfer catalyst.

11. A process of claim 4 wherein said reaction mixture is reacted at about 75°–180° C., said R's are tert-butyl, and said solubilizing agent is dimethyl sulfoxide.

12. A process for preparing high yields of methyl β-(3,5-di-tert-butyl-4-hydroxyphenyl)propionate consisting essentially of the steps of:
  (a) forming a mixture of (i) about one mole part 2,6-di-tert-butylphenol, (ii) an alkaline catalyst in an amount sufficient to form an alkali metal phenolate reactive intermediate and (iii) a solubilizing agent in an amount sufficient to solubilize said phenolate and increase the rate of reaction of said 2,6-di-tert-butylphenol with methyl acrylate; and
  (b) adding about one mole part methyl acrylate to said mixture over a period of less than 60 minutes to form as the major product methyl β-(3,5-di-tert-butyl-4-hydroxyphenyl)propionate; wherein the formation of undesirable by-products is reduced.

13. The process of claim 12 wherein said solubilizing agent is selected from aprotic polar solvents, phase transfer catalysts, and crown ethers.

14. The process of claim 12 wherein said catalyst is potassium tert-butoxide.

15. The process of claim 12 wherein said solubilizing agent is dimethyl sulfoxide.

16. The process of claim 15 wherein the mole ratio of dimethyl sulfoxide to potassium tert-butoxide is at least about 4:1.

17. The process of claim 12 carried out at about 100°–160° C.

18. The process of claim 12 wherein said catalyst amount is about 0.02 to 0.05 mole part and said solubilizing agent amount is about 0.10 to 1.00 mole part.

19. The process of claim 12 wherein the methyl acrylate is present in a slight molar excess of the 2,6-di-tert-butylphenol.

20. The process of claim 12 wherein said solubilizing agent is dimethylformamide.

21. The process of claim 12 wherein said solubilizing agent is $N(CH_2CH_2OCH_2CH_2OCH_3)_3$.

22. The process of claim 12 wherein said solubilizing agent is a crown ether.

23. The process of claim 14 wherein dimethyl sulfoxide is present in about 0.10–1.00 mole part.

24. The process of claim 23 wherein said process is carried out at about 100°–160° C.

* * * * *